United States Patent
Engel et al.

(10) Patent No.: US 10,399,288 B2
(45) Date of Patent: Sep. 3, 2019

(54) LAYING UNIT AND METHOD FOR PRODUCING A FIBRE COMPOSITE COMPONENT

(71) Applicant: Airbus Defence and Space GmbH, Taufkirchen (DE)

(72) Inventors: Franz Engel, München (DE); Christian Weimer, München (DE); Tilman Orth, München (DE)

(73) Assignee: Airbus Defence and Space GmbH (DE)

( * ) Notice: Subject to any disclaimer, the term of this patent is extended or adjusted under 35 U.S.C. 154(b) by 340 days.

(21) Appl. No.: 15/351,763

(22) Filed: Nov. 15, 2016

(65) Prior Publication Data
US 2017/0144386 A1 May 25, 2017

(30) Foreign Application Priority Data
Nov. 24, 2015 (EP) .................................... 15196030

(51) Int. Cl.
*B29C 70/38* (2006.01)
*B29K 105/06* (2006.01)

(52) U.S. Cl.
CPC ............ *B29C 70/382* (2013.01); *B29C 70/38* (2013.01); *B29C 70/384* (2013.01); *B29C 70/386* (2013.01); *B29C 70/388* (2013.01); *B29K 2105/06* (2013.01); *Y10T 156/1348* (2015.01); *Y10T 156/1788* (2015.01)

(58) Field of Classification Search
CPC ..... B29C 70/38; B29C 70/382; B29C 70/384; B29C 70/386; B29C 70/388; Y10T 156/1348; Y10T 156/1788
See application file for complete search history.

(56) References Cited

U.S. PATENT DOCUMENTS

| | | | |
|---|---|---|---|
| 6,968,883 B2 * | 11/2005 | Torres Martinez | ......................... B29C 53/8016 156/173 |
| 2006/0260751 A1 * | 11/2006 | Lauder | ................... B29C 70/388 156/382 |
| 2007/0272360 A1 * | 11/2007 | Santos Gomez | ......... B08B 1/02 156/441 |
| 2009/0301648 A1 * | 12/2009 | Hogg | .................... B29C 70/386 156/230 |
| 2014/0102625 A1 | 4/2014 | De Mattia | |
| 2015/0254835 A1 * | 9/2015 | Dorris | ................... G06T 7/0006 382/141 |

FOREIGN PATENT DOCUMENTS

| | | |
|---|---|---|
| DE | 20 2011 110 519 U1 | 7/2014 |
| DE | 10 2014 101447 A1 | 8/2015 |
| EP | 1 342 555 A1 | 9/2003 |

OTHER PUBLICATIONS

EP 15 196 030.9 Search Report dated May 25, 2016.

* cited by examiner

*Primary Examiner* — Carson Gross
(74) *Attorney, Agent, or Firm* — Lerner, David, Littenberg, Krumholz & Mentlik, LLP

(57) ABSTRACT

A laying unit for producing a fiber composite component is provided. The laying unit includes a housing and a plurality of fiber coils which are designed so as to be able to be unwound during a movement of the laying unit, wherein the fiber coils are provided in a movably mounted manner inside the housing.

21 Claims, 8 Drawing Sheets

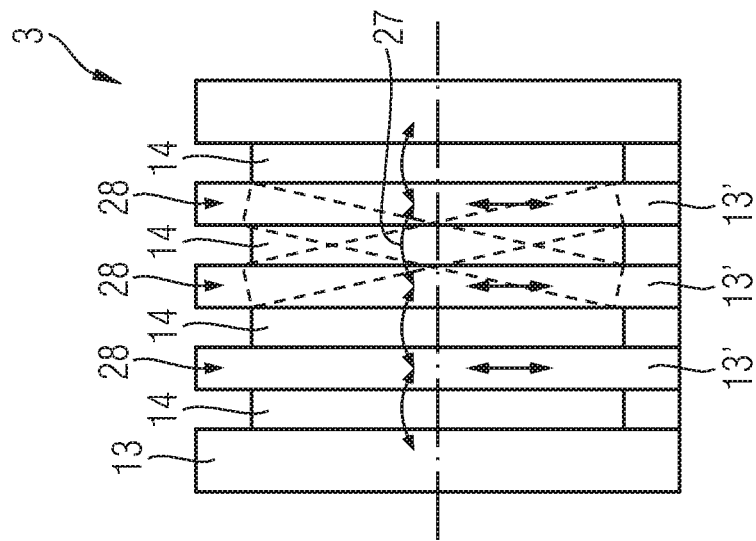
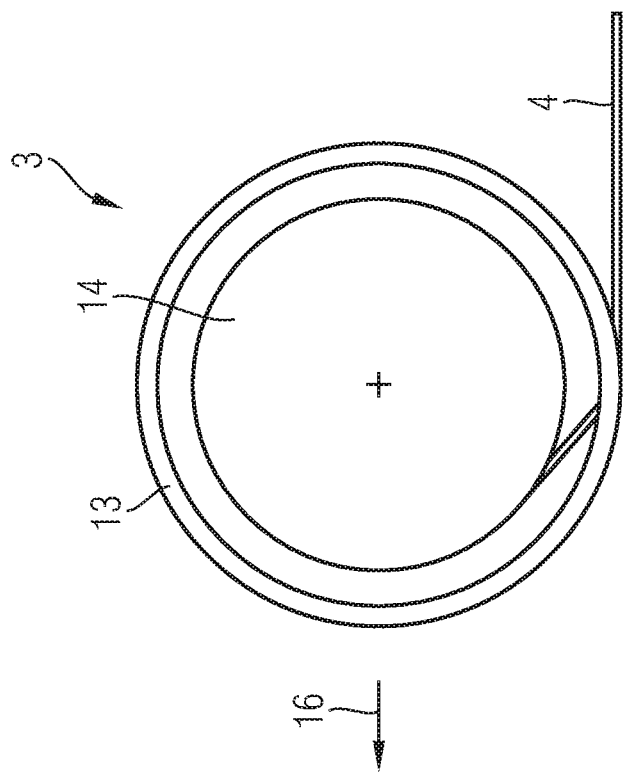
Fig. 1B
Fig. 1A

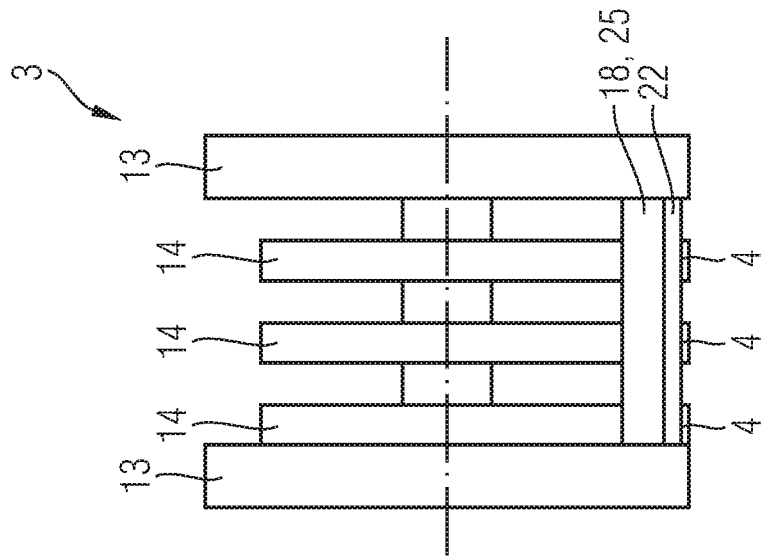
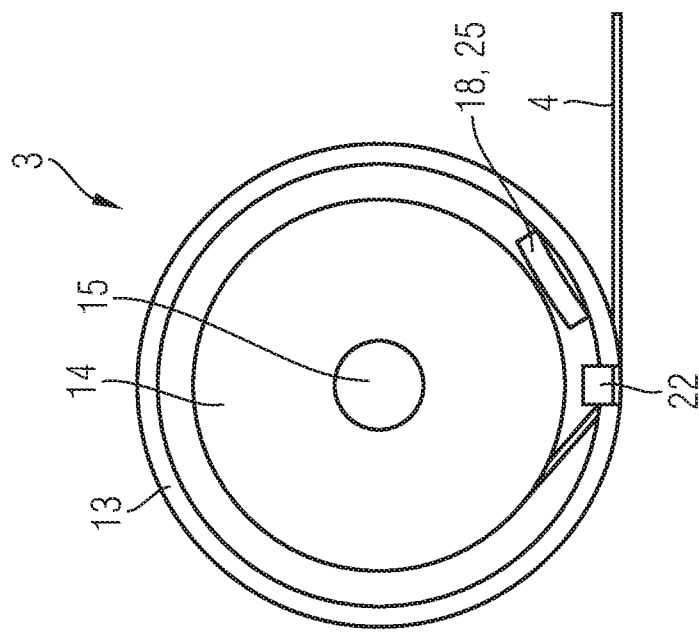

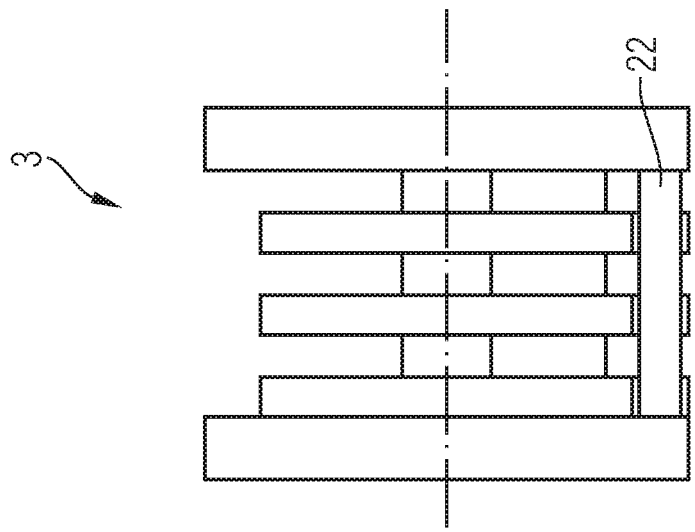
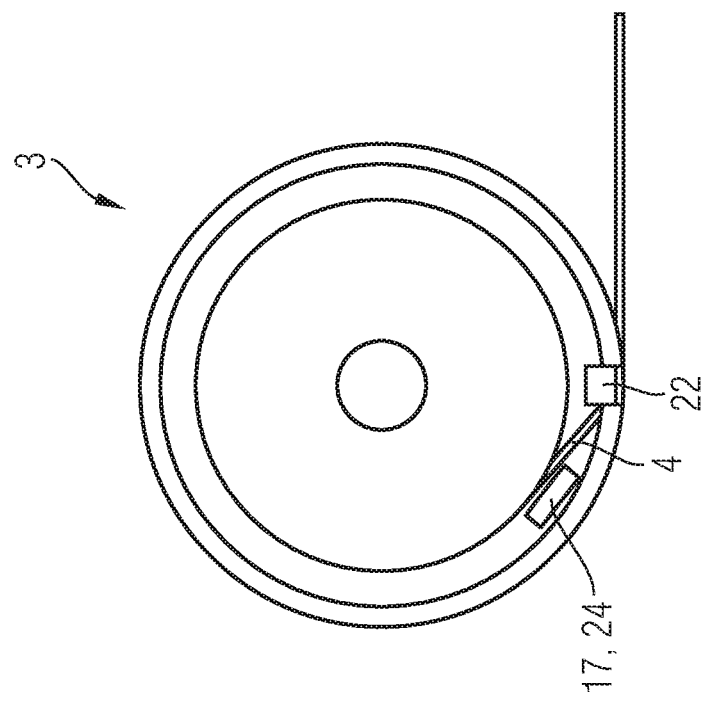

LAYING UNIT AND METHOD FOR PRODUCING A FIBRE COMPOSITE COMPONENT

FIELD OF THE INVENTION

The present invention relates to a laying unit and to a method for producing a fibre composite component.

Although the present invention can be applied to any fibre composite materials and any components, said invention and the problem addressed thereby will be described in greater detail with reference to carbon-fibre-reinforced plastics materials (CFRP) and large components, for example fuselage parts of an aircraft or spacecraft.

BACKGROUND OF THE INVENTION

Sometimes, large CFRP components are mostly produced using what is known as automated fibre placement (AFP) technology. For this purpose, system technology having very large dimensions is required. Said technology is mostly a laying robot which runs in a suspended manner on a gantry, what is known as a fibre-placement head or tape-laying head, which lays fibres on a shaping tool, for example the negative form of a fuselage portion of an aircraft or spacecraft. In this case, by passing over the tool, a wide laying web comprising a plurality of (for example 32) fibre webs or tapes that are in parallel and directly adjacent to one another is laid.

One approach to a fibre-laying apparatus which differs from such installations is described in DE 20 2011 110 519 U1. In this case, a rail system comprising a plurality of rails and a plurality of laying robots is provided, which can be moved along the rails on the rail system. The laying robots and the rail system are controlled by means of a central master computer. The laying robots are each configured to lay an individual object in the form of a roving or a sliver on a tool.

BRIEF SUMMARY OF THE INVENTION

One of the ideas of the present invention is to provide an improved laying unit and an improved method for producing a fibre composite component.

According to some aspects, the following is provided:

A laying unit for producing a fibre composite component, comprising: a housing and a plurality of fibre coils which are designed so as to be able to be unwound during a movement of the laying unit, wherein the fibre coils are provided in a movably mounted manner inside the housing.

A method for producing a fibre composite component, comprising the following method steps: Providing a shaping tool and a laying unit, in particular a laying unit according to the invention, wherein the laying unit comprises a plurality of fibre coils which are at a lateral distance from one another; laying fibre material by means of the laying unit, wherein the fibre material is unwound from the fibre coils and laid on the shaping tool in the form of a plurality of laying webs, wherein the laying webs are laid, at least in part, at a distance from one another with an intermediate space; laterally repositioning the laying unit by a width of a laying web; and re-laying fibre material by means of the laying unit on the shaping tool in the intermediate space.

A concept on which the present invention is based consists, in the case of a laying unit, in depositing a plurality of fibre coils, which can be unwound or unrolled during a movement of the laying unit, inside a housing so as to be movable and/or at a lateral distance from one another.

The fibre coils are in some embodiments mounted in such a way that they can be moved independently of one another. Furthermore, the fibre coils are for example designed and arranged so as to be able to be unwound simultaneously during a movement of the laying unit.

Thus, according to an aspect of the invention, it is possible to adapt the manner of depositing fibres by the laying unit to uneven and/or complex tool geometries, wherein a plurality of laying webs of the fibre material, in particular what are known as fibre tows (fibre cables), rovings (fibre strands) or fibre tapes (slivers), can still be laid at the same time in one operation.

In some embodiments, the fibre coils are mounted at a distance from one another, in particular they are at a distance from one another which is equal to the width of a laying web or a fibre tow, roving or tape.

The fibre material is therefore laid in two work steps. After a first laying step, in which a plurality of laying webs are accordingly laid at a distance from one another with an intermediate space, a second laying step takes place which is laterally offset by the width of a laying web in the intermediate space of the laying webs.

Due to the movable mounting thereof, the fibre coils can be oriented so as to be adapted to irregularities or double curvatures in the tool surface. Advantageously, this is not required as much by comparison with a single deposit of the fibre tows, rovings or tapes, even on a tool comprising irregularities and/or double curvatures.

The laying unit can be a mechanically independent and/or autonomously moving laying unit or a laying unit of a fibre-placement or tape-laying head of an AFP installation.

The housing can be any type of mechanical housing. The housing can be closed or can be open on one or more sides. In particular, in the case of a cylindrical housing, a lateral surface can be provided in such a way that it is cut out in part or in full. A frame-like design of the housing which is open on all sides is also possible. Furthermore, the housing can be in a single line or can be divided into a plurality of housing portions. In particular, the housing can have two end-face end portions, wherein the fibre coils are arranged therebetween. Furthermore, housing portions can be provided in the region of an intermediate space between the fibre coils.

Inside the housing, there is a retaining device or mounting device on which the fibre coils are mounted. The fibre coils can each be provided so as to be mounted separately or together on the retaining device or mounting device in the housing. The movability of the fibre coils can be achieved by means of a movability of the fibre coils relative to the retaining device and/or by means of a movability of the retaining device relative to the housing.

The movability of the fibre coils is provided as a rotational movability, that is to say a pivotability or tiltability. Alternatively or additionally, a translational movability (deflectability) can be provided. In this case, it is for example always possible to unwind or unroll the fibre coils during a movement of the laying unit.

An unwinding or unrolling of the fibre coils can be brought about by the movement of the laying unit. In this case, the fibre coils are mounted so as to be able to rotate freely around the shaft thereof. Alternatively or additionally, the unwinding can also be driven by means of a motor and/or mechanically by means of a transmission.

Advantageous embodiments and improvements of the invention are set out in the dependent claims.

According to some developments, an intermediate space is provided between each of the fibre coils, at least portions of which space form a movement space for the adjacent fibre coils. The fibre coils can be moved inside the movement space. Advantageously, each fibre coil can thus be moved independently. The fibre material can thus be laid with each fibre coil in a different orientation.

According to an advantageous embodiment, the fibre coils are each provided so as to be able to be tilted into an inclined position independently of one another. The inclined position is possible in particular by means of tilting around a shaft which extends in parallel with a movement direction of the laying unit. Other or additional tilting axes are alternatively or additionally possible. Advantageously, irregularities or double curvatures in a running surface, in particular of a tool, on which the laying unit runs can thus be compensated for by movement of the fibre coils. It is thus also possible to deposit fibres on tools having complex shapes or irregularities.

According to one embodiment, housing portions which can each be radially displaced independently of one another are provided in the region of the intermediate space of the fibre coils. The housing portions cover each of the intermediate spaces towards the outside and are provided so as to be displaceable in the radial direction relative to the fibre coils and/or to a shaft of the housing. In this case, the radial direction denotes a radial direction of the fibre coils and/or a radial direction based on a shaft of the housing, which has in particular a cylindrical design. Advantageously, by means of the radial displaceability, the level of the housing portions can be varied, for example when a tool has irregularities. As a result, the fibre material of the individual coils can be deposited in different orientations, which makes it possible to carry out depositing in accordance with irregularities, in particular even in the case of tools having double curvatures.

According to one embodiment, the fibre coils are designed to tilt into a suitable inclined position in accordance with a radial displacement of the housing portions. In particular, the fibre coils are designed to be operatively connected to the housing portions for this purpose. For example, an articulated connection, a connection by means of tie rods or by means of resilient connecting elements between adjacent fibre coils and housing portions can be provided. Thus, advantageously, the fibre coils are automatically tilted in an adapted manner, for example when an irregularity in a tool, which leads to the radial displacement of a housing portion, is passed over by the laying unit.

According to one development, the fibre coils are each mounted so as to be able to be tilted on a common shaft. In particular, for each fibre coil, the common shaft comprises one receiving portion, which is designed in each case to mount the fibre coil in a movable manner. In this case, so that the fibre coils can be exchanged in a relatively simple manner, an intermediate sleeve can be provided which is mounted on the receiving portion and receives the fibre coil in an easily exchangeable manner. Advantageously, a simple implementation of the movable mounting is thus provided.

According to one embodiment, a heating device is provided for activating a resin or binder of the fibre material to be laid from the fibre coils. For example, an LED, a laser diode and/or a heating spiral can be provided as the heating device. Alternatively or additionally, it is also possible to carry out heating by means of supplied heating gas, wherein the heating device is provided as a heating gas nozzle, infrared light, wherein the heating device is provided as an infrared lamp, or induced eddy currents, wherein the heating device is provided as a magnet. Advantageously, the binder or the resin is thus activated locally and directly during the laying of the fibre material. Thus, the fibre material can be prestabilised for example directly during the production as a preform. By means of the heating device, the tool and/or the fibre material to be laid can be heated directly before, during or after the deposition process.

According to another embodiment, an actuator is provided for pretreating a fibre layer of the fibre material. In this case, the fibre layer can be influenced for example with respect to the width thereof. Furthermore, it is conceivable to remove any impurities just before depositing the fibre layer. It is also conceivable to cut and/or split (splice) the individual fibres or the fibre layer. Alternatively or additionally, an actuator is provided for pretreating the surface of a tool on which the fibre material is to be laid. Said actuator can be used for example to preclean the surface. The quality of the fibre deposit is thus advantageously increased.

According to an advantageous embodiment, a depositing device is provided for laying in a defined manner at least one fibre layer of the fibre material (4). In this case, the depositing device positions the fibre material unwound from the plurality of fibre coils on a tool. Laying in a defined manner can be provided in particular as precise positioning of the fibre material in a predetermined position on the tool. Alternatively or additionally, the depositing device is provided for compacting at least one fibre layer of the fibre material. Advantageously, the fibre material is thus laid in a compact manner, which makes it possible to produce a fibre composite component having an increased fibre volume content.

According to one development, the depositing device is formed integrally with the heating device. This is possible in particular in the case of a magnetic depositing device. It is thus possible to lay the fibre material and activate the binder or resin at the same time.

According to another embodiment, a sensor in front of the depositing device is provided for measuring the fibre quality of the fibre material before the laying thereof. The quality of fibre material to be laid is thus advantageously ensured. The sensor can be a wide variety of sensor types, for example a laser light section sensor, a polarised light sensor, a contact image sensor (CIS), or the like. The sensor can be used to detect individual or several different quality factors, for example to measure the width, the weight of a fibre strand, or a degree of resin wetting of the fibre layer to be laid. Furthermore, contaminants, for example foil residues from a backing paper, can be detected. Alternatively or additionally, the sensor in front of the depositing device is provided for measuring the suitability of the surface of a tool or component, on which the fibre material is to be laid. It is thus ensured that a depositing process is only carried out on a suitable substrate, in particular a tool. In this case, for example defects or impurities on the surface can be detected. It is thus possible to react to such defects or impurities by means of the control unit of the laying unit. Firstly, the depositing process can be interrupted, and a warning message can be output to an operator. Secondly, a path correction of the depositing process can be carried out, in particular in an automated manner. Furthermore, it would be conceivable to introduce a countermeasure in an automatically or manually controlled manner. For example, an actuator for cleaning, in particular a cleaning nozzle which is provided on the laying unit for outputting compressed air to remove an impurity, can be activated.

According to yet another embodiment, a sensor trailing the depositing device is provided for detecting the arrangement and/or quality of the deposition of the fibre material.

The quality of laid fibre material is thus advantageously ensured. In this case as well, the sensor can be a wide variety of sensor types, for example a laser light section sensor, a polarised light sensor, a contact image sensor (CIS), or the like. In particular, flaws in the deposition, such as gaps between the fibre layers or tapes, intertwining (what are known as twists), splitting in the fibre strand (what is known as splicing), undesirable overlapping or undesirable knotting (what are known as fuzzballs) and any foil residues, can thus be detected.

According to one embodiment, the depositing device is formed integrally with a drive device for moving the laying unit. Advantageously, the depositing device thus additionally takes over the function of transmitting power to the running surface. In addition, the heating device can also be formed integrally therewith.

According to one development, the drive device is provided inside the housing. In this case, the housing can be in the form of a rolling surface for moving the laying unit. Advantageously, the housing thus has a dual function, and an additional rolling surface of the drive device is not required. For this purpose, the housing in some embodiments has a cylindrical or different type of round shape. In another embodiment, the drive device can be in the form of a drive roll provided outside the housing. In this case, the drive roll can provide additional stabilisation of the laying unit. In this case, the housing can have any shape which is suitable for receiving the fibre coils.

The configurations and developments above can be combined with one another as desired where appropriate. Furthermore, all the features of the laying unit can be transferred to the method for producing a fibre composite component.

Further possible configurations, developments and implementations of the invention also do not comprise explicitly mentioned combinations of features of the invention described previously or in the following with respect to the embodiments. In particular, in the process a person skilled in the art will also add individual aspects as improvements or additions to the particular basic form of the present invention.

BRIEF DESCRIPTION OF THE DRAWINGS

The invention will be described in greater detail on the basis of embodiments, with reference to the accompanying figures of the drawings. The elements of the drawings are not necessarily shown to scale with respect to one another.

In the drawings:

FIG. 1A is a schematic side view of a laying unit;

FIG. 1B is a schematic front view of the laying unit according to FIG. 1A;

FIG. 3A is a schematic side view of a laying unit according to another embodiment;

FIG. 3B is a schematic front view of the laying unit according to FIG. 3A;

FIG. 4A is a schematic side view of a laying unit according to yet another embodiment;

FIG. 4B is a schematic front view of the laying unit according to FIG. 4A;

In the figures, the same reference numerals denote like or functionally like components, unless stated otherwise.

DETAILED DESCRIPTION

Figure 2B:
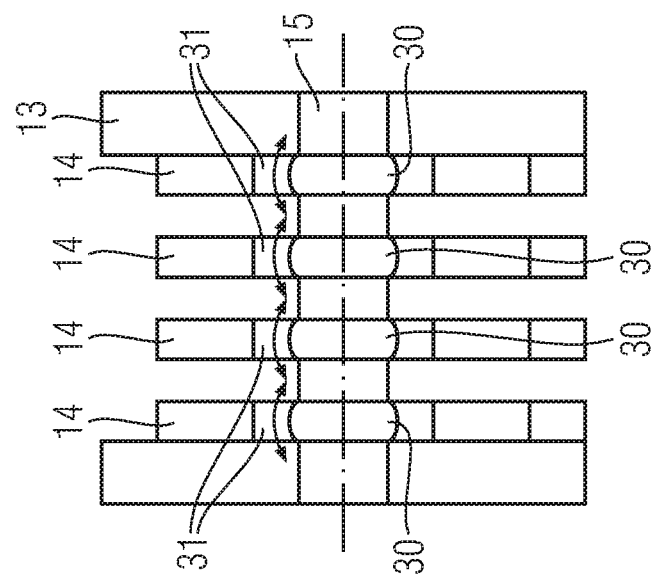
FIG. 2B is a schematic cross-sectional view of the laying unit according to FIG. 2A.

FIG. 1A is a schematic side view of a laying unit 3.

The laying unit 3 comprises a housing 13, inside which a plurality of fibre coils 14 are mounted.

Fibre material 4 can be unwound from each fibre coils 14 at the same time. For example, during a movement of the laying unit 3, the fibre material is unwound in a movement direction 16 by means of a tensile force acting on the fibre material 4, which force is brought about by the movement. The unwound fibre material 4 is laid directly on a tool (not shown in this case).

In the embodiment shown, the housing 13 is a cylindrical housing which unrolls to move the laying unit 3 on the lateral surface thereof.

FIG. 1B is a schematic front view of the laying unit according to FIG. 1A.

The cylindrical housing 13 is provided so as to be cut out in part in the region of the fibre coils 14 on the lateral surface thereof.

The fibre coils 14 are mounted in such a way that they can be moved inside the housing 13 and can be tilted into an inclined position independently of one another. Furthermore, they are arranged side-by-side along the shaft of the cylindrical housing 13 and at a distance from one another with an intermediate space 28 in each case.

In this case, the intermediate space 28 forms portions of a movement space 27 of the adjacent fibre coils 14, inside which the fibre coils 14 can be moved. The movability of the fibre coils 14 is symbolised by the marked arrows. One of the fibre coils is shown by way of example, by means of dashed lines, as being tilted into an inclined position on both sides.

In the region of each intermediate space 28, housing portions 13' which cover the intermediate spaces 28 towards the outside are provided. The housing portions 13' can each be radially displaced individually relative to the fibre coils 14 and/or to a shaft of the cylindrical housing 13.

The fibre coils 14 are designed to be operatively connected to the housing portions 13'. For example, the operative connection can be established by means of tie rods, articulated arms, resilient connecting elements or the like, which are distributed over the periphery of the housing portions 13 and connect the respective fibre coils 14 to the respective housing portions 13'. Accordingly, due to the operative connection to the housing portions 13', the fibre coils 14 tilt in a manner which is always adapted to a radial displacement of the housing portions 13' into an inclined position which is suitable therefor. The fibre material is thus laid in accordance with an irregularity.

A drive device, which is not shown here for the sake of greater clarity, is for example integrated in the housing 13. In particular, a drive device can be integrated in the region of each end face of the housing 13. It is additionally possible to provide some or all of the housing portions 13' with a drive device. Alternatively or additionally, a drive device can also be provided which extends over the entire width of the laying unit 3. Furthermore, a drive roll which is provided outside the housing can alternatively or additionally be provided as the drive apparatus. The possible design and mode of operation of the drive apparatus will be described in greater detail with reference to FIGS. 5, 6 and 7.

Figure 2A:
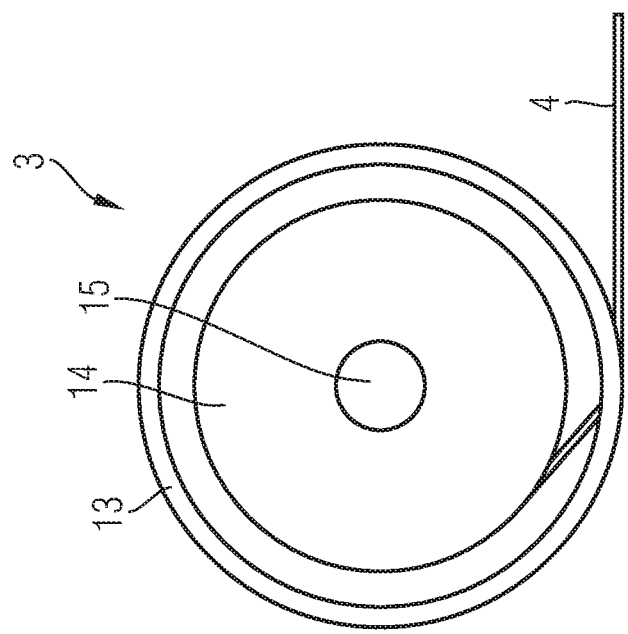
FIG. 2A is a schematic side view of a laying unit according to one embodiment.

FIG. 2A is a schematic side view of a laying unit 3 according to one embodiment.

In this case, the laying unit 3 has a common shaft 15, on which the fibre coils 14 are intended to be mounted.

FIG. 2B is a schematic cross-sectional view of the laying unit 3 according to FIG. 2A. In the view shown, the housing portions 13' are hidden for the sake of greater clarity.

The common shaft 15 is mounted in the housing 13 and comprises one receiving portion 30 for each fibre coil 14, which portion is designed in each case for mounting the fibre coil 14 in a movable manner.

An intermediate sleeve 31 is provided on each of the receiving portions 30, which sleeve is provided so as to be able to be tilted into an inclined position relative to each receiving portion 30. For this purpose, the receiving portion 30 comprises a convex outer face. The fibre coil 14 is mounted on the intermediate sleeve 31 in an axially secured manner in each case. The intermediate sleeve 31 provides a contact surface which corresponds to an inner contact surface of the fibre coils 14. For example, said contact surfaces can be cylindrical. The fibre coils 14 are thus easy to exchange.

In another embodiment, the fibre coils 14 can also be provided so as to be received directly on the receiving portion 30, without an intermediate sleeve 31. In this case, axial safeguarding against an axial displacement of the fibre coils 14, for example in the form of spacer sleeves, is additionally provided.

In yet another embodiment, the shaft 15 can be in the form of a continuously cylindrical shaft, wherein the receiving portions 30, which provide the tiltability, are provided so as to be integrated in the fibre coils. In this case, the fibre coils can be threaded onto the shaft 15, for example with spacer sleeves arranged therebetween in each case, to provide the intermediate spaces 28.

FIG. 3A is a schematic side view of a laying unit 3 according to yet another embodiment.

In this embodiment, a depositing device 22 is provided for laying in a defined manner and/or for compacting the fibre material 4. The depositing device 22 is mounted on the housing.

Furthermore, in this embodiment, a sensor 18 trailing the depositing device 22 and a heating device 25 are provided.

The trailing sensor 18 is provided for detecting the arrangement and/or quality of the deposition of the fibre material 4. The trailing sensor 18 can be a wide variety of sensor types. For example, a laser light section sensor, a polarised light sensor, a contact image sensor (CIS), or the like can be provided. Flaws in the deposition of the fibre material 4 can thus be detected. For example, flaws in the laid fibre material 4 which can be detected by means of the sensor 18 can be gaps between the laid fibre layers or strips (tapes), intertwining (what are known as twists), splitting in a fibre strand (what is known as splicing), undesirable overlapping or undesirable knotting (what are known as fuzzballs) and any undesirable foil residues.

In this case, the heating device 25 is arranged by way of example in a common housing with the trailing sensor 18. Equally, separate housings can also be provided for the heating device 25 and the trailing sensor 18.

The heating device 25 is provided for activating a resin or binder of the fibre material 4 to be laid from the fibre coils 14. For example, an LED, a laser diode and/or a heating coil can be provided as the heating device. Alternatively or additionally, it is also possible to heat the fibre material 4 by means of externally supplied heating gas. In this case, the heating device 25 is in the form of a heating gas nozzle. Furthermore, the heating device 25 can be an infrared lamp for emitting infrared light or a magnet for inducing eddy currents in a ferromagnetic tool surface. By means of the heat from the heating device 25 acting on the fibre material, a binder or a resin is activated locally and directly, before, during or after laying the fibre material 4. Thus, the fibre material 4 which is laid, for example in the form of a fibre cluster, can be prestabilised as a preform.

FIG. 3B is a schematic front view of the laying unit 3 according to FIG. 3A. In this view, the housing portions 13' are hidden for the sake of greater clarity.

In this case, the depositing device 22 extends by way of example continuously over the entire region of the fibre coils 14. Alternatively, a separate, individually assigned depositing device 22 can be provided for each fibre coil 14. In this case, the depositing device 22 assigned to a fibre coil is tilted together with the fibre coils 14.

The depositing device 22 is for example in the form of a magnet which interacts with a tool surface, which magnet presses the fibre material 4 onto a tool surface which interacts therewith in a magnetic manner. In the case of such a magnetic design of the depositing device, said device can also simultaneously be in the form of a drive device.

The trailing sensor 18 and the heating device 25 likewise extend over the entire width of the region of the fibre coils 14 between the end-face portions of the housing 13. Alternatively, a separate, individually assigned trailing sensor 18 and/or a separate, individually assigned heating device 25 can also be provided in this case for each fibre coil 14.

FIG. 4A is a schematic side view of a laying unit 3 according to another embodiment. FIG. 4B is a schematic front view of the laying unit 3 according to FIG. 4A.

In this embodiment, a sensor 17 in front of the depositing device 22, and an actuator 24 are provided. By way of example, the forward sensor 17 and the actuator 24 are arranged in a common housing. Equally, separate housings can be provided for the sensor 17 and the actuator 24.

The forward sensor 17 is used to measure the fibre quality of the fibre material 4 before the laying thereof. The sensor 17 can be a wide variety of sensor types, for example a laser light section sensor, a polarised light sensor, a contact image sensor (CIS), or the like.

By means of the sensor 17, individual or several different quality factors can be detected. For example, a measurement of the width, the weight of a fibre strand, or the degree of resin wetting of the fibre layers to be laid of the fibre material 4 can be provided for each fibre coil separately or for all the fibre coils together. Furthermore, by means of the sensor 17, contaminants in the fibre material 4, such as foil residues from a backing paper, can also be detected before the laying thereof.

Alternatively or additionally, the forward sensor 17 is provided for measuring the suitability of the surface of a tool on which the fibre material 4 is to be laid. It is thus ensured that a depositing process is only carried out on a suitable substrate, in particular the tool. In this case, for example defects or contaminants/impurities on the surface of the tool can be detected. It is thus possible to react to such defects or contaminants.

Firstly, in response, the process of depositing the fibre material 4 can be interrupted, and a warning message can be output to an operator. Secondly, a path correction of the process of depositing the fibre material 4 can be carried out, in particular in an automated manner. Furthermore, in response, a countermeasure can be introduced in an automatically or manually controlled manner by means of the actuator 24. For example, the actuator 24 can be in the form of a cleaning nozzle for outputting compressed air to remove an impurity. When a contaminant has been detected, the actuator 24 can thus be activated to clean the tool surface. Alternatively, the actuator can also be a mechanical actuator, for example a cleaning brush.

Furthermore, the actuator 24 can alternatively or additionally be designed to pretreat a fibre layer 4' of the fibre material 4 for each fibre coil individually or for all the fibre coils together. In this case as well, designing the actuator 24 as a cleaning nozzle for cleaning the fibre layer 4' is also considered.

Figure 5:
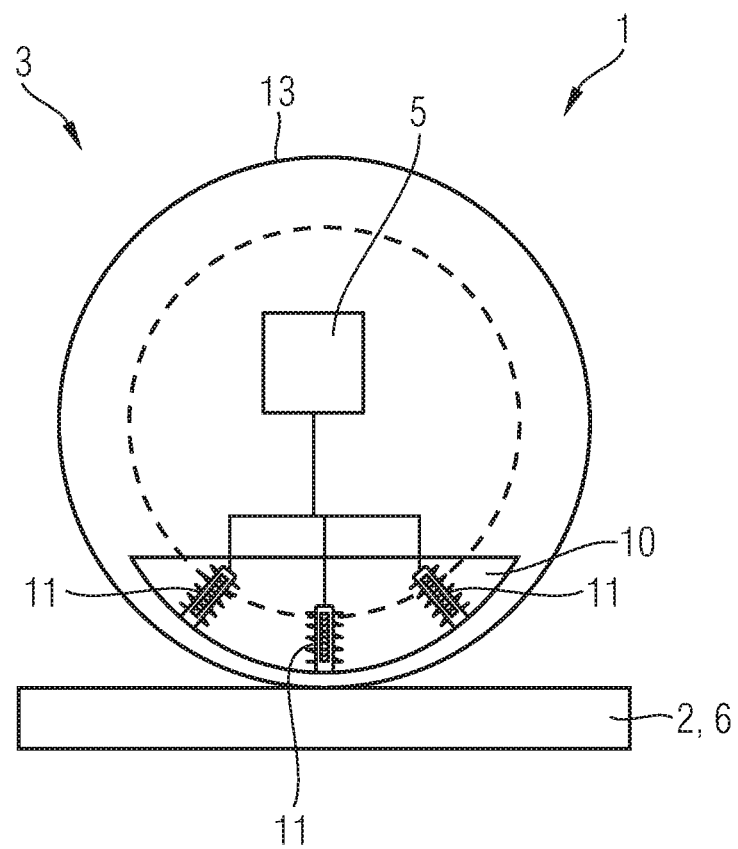
FIG. 5 is a schematic sectional view of an embodiment of an apparatus for producing a fibre composite component.

FIG. 5 is a schematic sectional view of an embodiment of an apparatus 1 for producing a fibre composite component.

The apparatus 1 comprises a laying unit 3 and a shaping tool 2. The laying unit 3 can be a laying unit 3 which is designed according to any of FIGS. 1 to 4B.

The shaping tool 2 is in the form of a ferromagnetic running surface 6 for the laying unit 3.

The laying unit 3 comprises a cylindrical, in particular circular cylindrical, housing 13. Inside the housing 13, a drive device 10 which movably runs along the inner wall of the housing 13 is provided. The drive device 10 is accordingly intended to be arranged inside the housing 13. In this case, the housing 13 is in the form of a rolling surface for moving the laying unit 3.

The drive device 10 is in the form of a pendulum in the shape of a cylinder portion, which pendulum can move in the peripheral direction of the housing 13, and comprises individually actuable magnets 11 which act in different radial directions.

If the drive device 10 is displaced with respect to the orientation thereof relative to the housing 13 by means of an interaction of the magnets 11 with the ferromagnetic running surface 6, this also makes the housing 13 follow or roll in the direction of the drive device 10.

The magnets 11 are correspondingly actuated by means of a control device 5 in order to move the laying unit 3.

As an alternative to a freely movable pendulum, guiding apparatuses, for example a rail system or the like, can also be provided on the inner face of the housing 13 to guide the drive device 10.

The drive device 10 shown here by way of example can be arranged at different points on the housing 13 of a laying unit 3. A plurality of drive devices 10 of this type can also be provided.

Furthermore, it is conceivable to provide a drive apparatus 10 of this type, instead of in a cylindrical housing 13 of a laying unit 3, in a cylindrical drive roll which is arranged outside the housing 13, in the same way.

Figure 6:
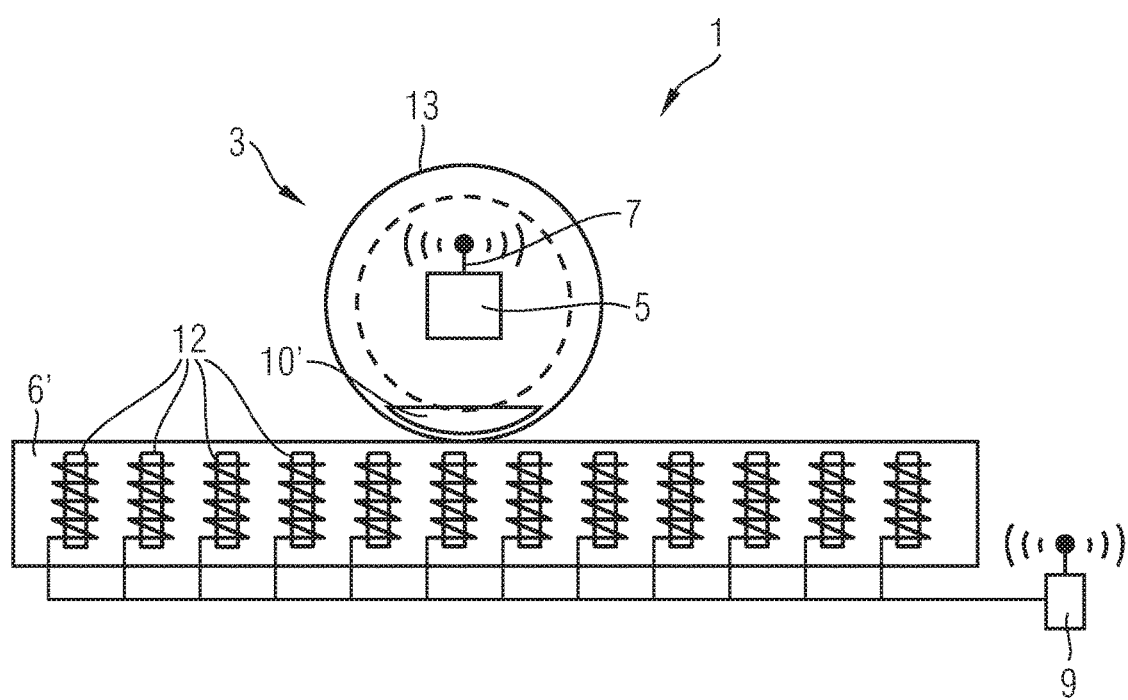
FIG. 6 is a schematic sectional view of another embodiment of an apparatus for producing a fibre composite component.

FIG. 6 is a schematic sectional view of another embodiment of an apparatus 1 for producing a fibre composite component.

The apparatus 1 comprises a laying unit 3, which can likewise be a laying unit 3 which is designed according to any of FIGS. 1 to 4B.

In this embodiment, the running surface 6' comprises a plurality of controllable magnets 12. The laying unit 3 comprises a drive device 10' which interacts therewith and which is likewise provided, by way of example, as a freely movable pendulum which can be moved along the inner face of the housing. In this case, the pendulum is designed in particular as a ferromagnetic mass element. Alternatively or additionally, permanent or controllable magnets can also be provided in an integrated manner in the drive device 10'.

The controllable magnets 12 are coupled to a receiving unit 14, which is configured to relay control commands from the control device 5 of the laying unit 3 to the individual magnets 12. The control device 5 is coupled to communication means 7 of the laying unit 3 so that control signals can be transmitted to the receiving device 14.

The control device 5 is thus configured to actuate the controllable magnets 12 individually in a way which is suitable for moving the laying unit 3 and thereby generate a magnetic field to attract the drive device 10'. If the drive device 10' is attracted by a magnet 12 which is arranged at the side thereof, said device is deflected out of an idle position relative to the housing 13 of the laying unit 3. The housing 13 and, together therewith, the entire laying unit 3, are thus made to follow or roll in the direction of the magnet 12 currently generating the magnetic field.

In order to move the laying unit 3, the magnets 12 are actuated by means of the control apparatus 5 according to the desired movement of the laying unit 3.

The drive device 10 shown here by way of example can also be arranged at different points on the housing 13 of a laying unit 3. A plurality of drive devices 10 of this type can also be provided.

Furthermore, it is also conceivable to provide a drive apparatus 10 of this type, instead of in a cylindrical housing 13 of a laying unit 3, in a cylindrical drive roll which is arranged outside the housing 13, in the same way.

Figure 7:
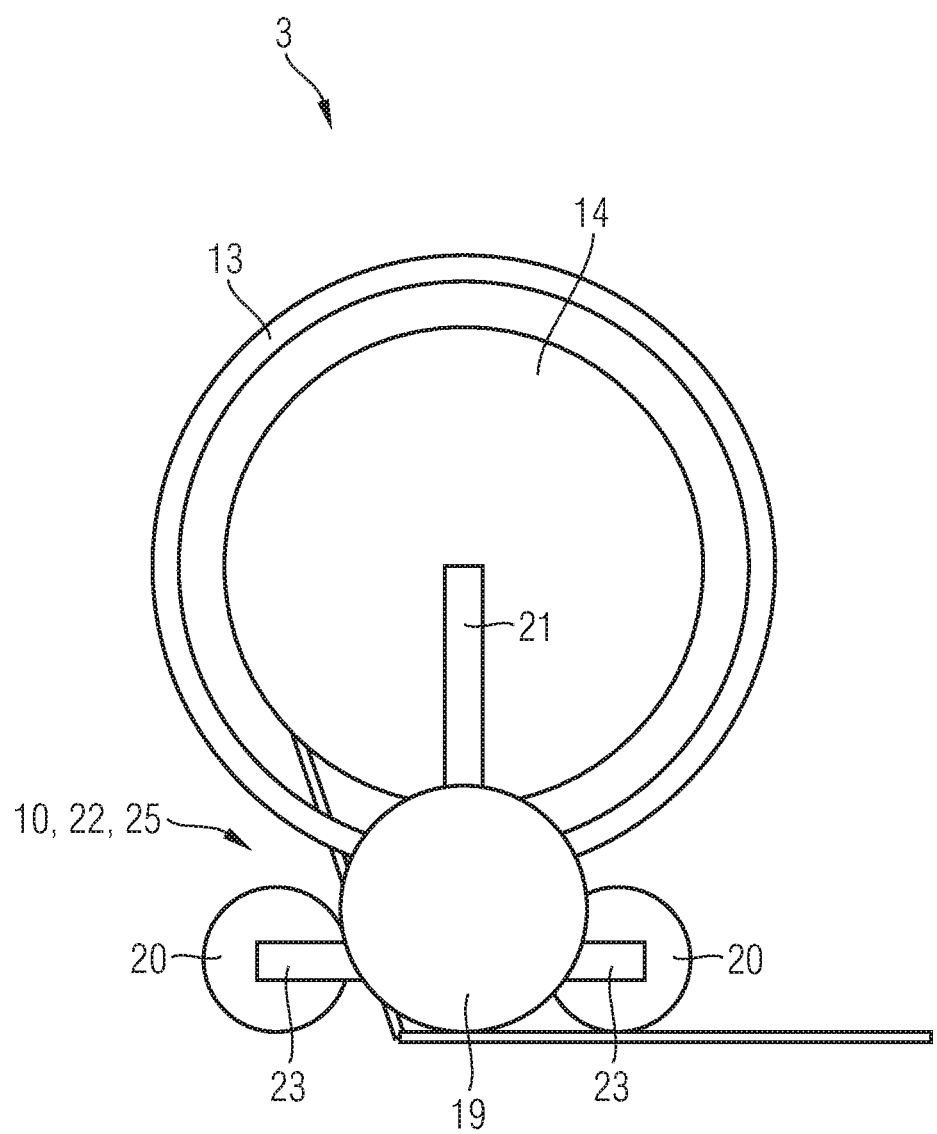
FIG. 7 is a schematic side view of a laying unit according to another embodiment.

FIG. 7 is a schematic side view of a laying unit 1 according to another embodiment.

In this case, the drive device 10 is in the form of a drive roll 19 which is coupled to the housing 13. The drive roll 19 can have the same operating principle as the drive device 10 or 10' shown in FIG. 5 or 6, wherein a magnetic or ferromagnetic pendulum runs inside the drive roll 19.

Alternatively or additionally, a plurality of radially oriented electromagnets can also be integrated in the drive roll 19, wherein, in each case, a magnet which is suitably oriented to interact with the running surface is actuated for movement.

Furthermore, permanent magnets and/or a ferromagnetic material can alternatively or additionally be provided so as to be integrated in the drive roll 19, wherein a drive of the drive roll 19 is provided by means of a magnetic field which can be energised by an assigned running surface which is provided for the laying unit 3. For this purpose, the running surface can be provided with a plurality of controllable magnets, as described by way of example with reference to FIG. 6.

The drive device 10 is coupled to the housing 13 by means of a coupling device 21, and supports the housing 13. By contrast with the laying units 3 described previously, the housing 13 itself thus does not unroll on the running surface 6 for movement. This function is performed instead by the drive roll 19 and the support rolls 20.

In addition to the drive device 10, in this embodiment, the depositing device 22 is also formed by the drive roll 19. The depositing device 22 is used to lay in a defined manner and/or to compact a fibre layer of the fibre material 4. In this embodiment, the laying unit 3 can thus advantageously also be used to compact fibre material which has already been laid.

The forces that can be applied by means of the depositing device 22 for laying in a defined manner and/or compacting can be regulated or set by means of the strength of the magnetic field which is provided to move and/or hold the laying unit 3 on the running surface.

In this case, the trailing support roll 20 can be in the form of a trailing sensor system, which has the same function as the trailing sensor 18. Alternatively or additionally, the support rolls 20 can be provided to compact the fibre material 4.

The drive roll 19 is further provided as a heating device 25 for activating a resin or binder of a laid fibre layer of the fibre material 4. In particular, the drive roll 19 is provided with a magnetic drive which generates eddy currents in the drive roll and/or in the tool during the movement of the laying unit 3 if said drive roll and/or tool contain a ferromagnetic material. The eddy currents accordingly heat the drive roll and/or the running surface due to the electrical resistance. The heating device 25 is thus in the form of a drive roll 19 which heats up during movement and/or as a drive roll 19 which heats up the running surface.

In some embodiments, the drive roll 19 is intended to be integrated in the form of a depositing device 22 for laying in a defined manner and/or compacting, and as a heating device 25 for activating a resin or binder.

Figure 8:
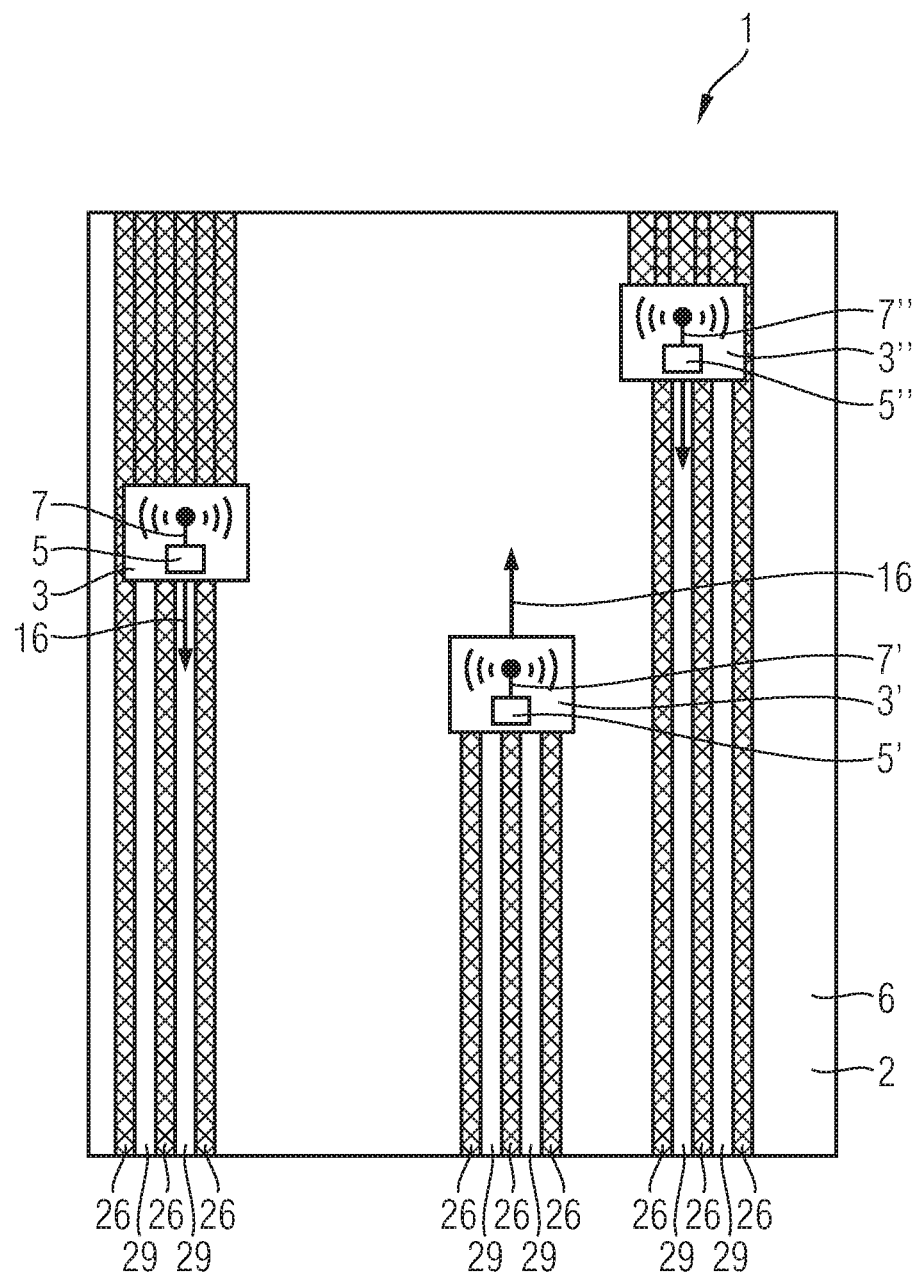
FIG. 8 is a schematic plan view of an apparatus for producing a fibre composite component.

FIG. 8 is a schematic plan view of an apparatus for producing a fibre composite component.

The apparatus 1 comprises a shaping tool 2 and a plurality of laying units 3, 3', 3". The tool 2 simultaneously represents a running surface 6 for the laying units 3, 3', 3".

The laying units 3, 3', 3" are designed according to any of the preceding FIGS. 1 to 7.

The laying units 3, 3', 3" are each designed to lay a fibre material 4 on the shaping tool 2. Said units each comprise a control device 5, 5', 5", which is configured to actuate each laying unit 3; 3'; 3" to automatically interact with the additional laying units 3, 3' 3" in order to lay a predetermined fibre arrangement together.

The laying units 3, 3', 3" are shown during the process of laying the fibre material 4, wherein three laying units 3, 3', 3" are shown purely by way of example. Rather than three, there can be any number of laying units 3, 3', ( . . . ), 3n.

The laying units 3, 3', 3" are each configured to move autonomously on the running surface 6. Said units accordingly comprise sensors (not shown in detail) and a drive device, which interact with the control apparatus 5, 5', 5" for autonomous movement. The sensors detect regions which have already been overlaid with fibre material 4, edge regions of the tool 2 and additional laying units. The laying units 3, 3', 3" each further comprise communication means 7, 7', 7" which are used for communication between the laying units 3, 3', 3". The pattern can thus be flexibly adapted or the fibre arrangement can be flexibly divided amongst the laying units 3, 3', 3" for laying said fibre arrangement.

A laying unit is actuated by the control device 5, 5'; 5" in such a way that the nearest portion of the tool 2, which is to be overlaid with a fibre layer of the fibre material 4, is overlaid in a manner that is geometrically simple to detect, in particular in a straight line.

Information is distributed by the communication means 7, 7', 7" between the laying units via portions which have already been overlaid. The movement paths of the laying units thus only cross if this is desirable for the pattern to be laid of the fibre arrangement, or if one laying unit moves to a new starting point.

The fibre material 4 is unwound by means of the laying units 3, 3', 3" during the movement thereof from the plurality of the fibre coils 14, of which each laying unit 3, 3', 3" has its own, and is laid on the shaping tool 2 in the form of a plurality of laying webs 26. In this case, the laying webs 26 are laid at a distance from one another with an intermediate space 29 due to the lateral spacing of the fibre coils 14.

With reference to the embodiment according to FIG. 1, if the tool 2 has an irregularity, at the location of the irregularity, the housing portions 13' are displaced in the radial direction in accordance with the irregularity. Furthermore, the fibre coils 14 are pivoted into an inclined position in accordance with the irregularity in order to deposit the fibre material 4 in a manner which is likewise adapted to the irregularity. The size of the intermediate space 29 can thus vary at the location of an irregularity. Furthermore, it is possible, when the fibre coils are completely tilted locally in the region of the irregularity, for there to no longer be an intermediate space.

In the case of reaching an edge or a limit of the tool 2 or a portion which has already been overlaid with fibre material 4 in the desired manner, the movement direction of the laying unit 3; 3'; 3" is changed, which is actuated by the control device, and the laying unit is repositioned laterally by a width of a laying web 26. For example, the depositing unit rotates with an offset of a width of a fibre layer or a laying web of the fibre material 4. Subsequently, during a movement in the opposite direction, fibre material 4 is laid again by means of the laying unit 3, such that it is offset by the width of a laying web, on the shaping tool 2, wherein the fibre material is laid in the intermediate space 27 of the previously laid laying webs 26.

If there are no free adjacent portions of the tool, the laying unit moves to a new starting point which has not yet been overlaid with a desired fibre layer.

The laying units 3, 3', 3" each comprise communication means 7, 7', 7". The starting point is for example selected on the basis of the information transmitted from the other laying units by the communication means at a point on the tool at which no deposit has taken place yet.

This procedure is continued in particular in an autonomous manner until there are no more free portions of the tool 2 at which the predetermined fibre arrangement plans for there to be a deposit. The entire shaping tool 2 is thus for example overlaid with fibre material 4.

Although the present invention has been described in the present case on the basis of some embodiments, it is not restricted to said embodiments, but rather can be modified in various ways.

For example, it is conceivable to provide the fibre coils as fibre-delivery spools or as fibre-deflecting coils. In the case of fibre-deflecting coils, an external fibre-feeding device is provided, which feeds the fibre material to the fibre coils. In this case, the fibre coils deflect the fibre material in accordance with irregularities on a tool.

For example, in addition, the drive device is not necessarily a pendulum. As an alternative or in addition to a pendulum, movable, controllable magnets can also be provided on a guide system which is provided inside the laying unit.

According to another embodiment, an outer skin or a layer of the laying unit which is provided close to an outer skin can be designed to be able to be magnetised by means of an actuation. In particular, actuable electromagnets can be provided to be integrated in the outer skin of the laying unit. In order to move the laying unit, the magnetic field is displaced by a corresponding actuation in the desired movement direction along the outer skin or magnetisable layer.

In addition to a controllable magnetic field, a permanently acting or static magnetic field can also be provided between the laying unit and the running surface. The laying unit can thus be held on the running surface regardless of the movement, for example it can operate even during overhead work. Furthermore, a compacting force applied by means of the laying unit to the fibre material can thus also be set to a predetermined value.

Instead of the common shaft 15, a different type of retaining device can be provided for the fibre coils, which mounts the fibre coils inside the housing 13. The retaining device retains or mounts the fibre coils and continually orients them according to requirements. The retaining device itself can be provided to be mounted in a fixed or movable manner inside the housing. The retaining device can in particular also be formed integrally with the drive device. For example, the retaining device can be designed as an inner housing which is provided with a slightly smaller diameter inside the housing 13 and which can be rotated relative to the housing 13. For example, for this purpose, said inner housing can be coupled to the housing 13 by means of mechanical or magnetic bearings. In particular cylindrical housings 13 are considered for such a configuration.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A laying unit for producing a fibre composite component, comprising:
    a cylindrical housing configured to unroll on a surface; and
    a plurality of fibre coils configured so as to be able to be unwound during a movement of the laying unit, wherein the fibre coils are provided in a movably mounted manner inside the housing.

2. The laying unit of claim 1, wherein an intermediate space is provided between each of the fibre coils, at least portions of space which form a movement space of adjacent fibre coils of the plurality of fibre coils, inside which the fibre coils can be moved.

3. The laying unit of claim 2, wherein the fibre coils are each configured so as to be able to be tilted into an inclined position independently of one another.

4. The laying unit of claim 1, further comprising, in a region of an intermediate space of the fibre coils, housing portions, each configured to be radially displaced independently of one another.

5. The laying unit of claim 4, wherein the fibre coils are configured so as to be tilted into a suitable inclined position in accordance with a radial displacement of the housing portions.

6. The laying unit of claim 5, wherein the fibre coils are each mounted so as to be able to be tilted on a common shaft.

7. The laying unit of claim 4, wherein the fibre coils are configured to be operatively connected to the housing portions.

8. The laying unit of claim 3, wherein the fibre coils are each mounted so as to be able to be tilted on a common shaft.

9. The laying unit of claim 1, further comprising a heating device for activating a resin or binder of a fibre material to be laid from the fibre coils.

10. The laying unit of claim 1, further comprising an actuator for pretreating a fibre layer of a fibre material.

11. The laying unit of claim 1, further comprising a depositing device for laying in a defined manner.

12. The laying unit of claim 11, wherein the depositing device is formed integrally with a heating device.

13. The laying unit of claim 11, further comprising a sensor in front of the depositing device for measuring a fibre quality of a fibre material before a laying process.

14. The laying unit of claim 11, further comprising a sensor trailing the depositing device for detecting an arrangement of deposition of a fibre material.

15. The laying unit of claim 11, wherein the depositing device is formed integrally with a drive device for moving the laying unit.

16. The laying unit of claim 15, wherein the drive device is provided inside the housing, and the housing is formed as a rolling surface for moving the laying unit, or the drive device is in the form of a drive roll coupled to the housing.

17. The laying unit of claim 11, further comprising a sensor in front of the depositing device for measuring a suitability of a surface of a tool on which a fibre material is to be laid.

18. The laying unit of claim 11, further comprising a sensor trailing the depositing device for detecting a quality of a deposition of a fibre material.

19. The laying unit of claim 1, further comprising an actuator for pretreating a surface of a tool on which a fibre material is to be laid.

20. The laying unit of claim 1, further comprising a depositing device for compacting at least one fibre layer of a fibre material.

21. A laying unit for producing a fibre composite component, comprising:
    a housing;
    a plurality of fibre coils configured so as to be able to be unwound during a movement of the laying unit, wherein the fibre coils are provided in a movably mounted manner inside the housing;
    a depositing device for laying in a defined manner,
    wherein the depositing device is formed integrally with a drive device for moving the laying unit, and
    wherein the drive device is provided inside the housing, and the housing is formed as a rolling surface for moving the laying unit, or the drive device is in the form of a drive roll coupled to the housing.

* * * * *